United States Patent [19]

Allison

[11] Patent Number: 4,857,066
[45] Date of Patent: Aug. 15, 1989

[54] SANITARY NAPKIN OR LIKE ARTICLE HAVING AN INTEGRAL CARRYING/DISPOSAL ENVELOPE

[75] Inventor: Kathleen S. Allison, Tacoma, Wash.

[73] Assignee: Weyerhaeuser Company, Tacoma, Wash.

[21] Appl. No.: 153,120

[22] Filed: Feb. 8, 1988

[51] Int. Cl.[4] .............................................. A61F 13/16
[52] U.S. Cl. .................................. 604/385.1; 604/386; 604/387; 306/438; 306/621
[58] Field of Search ............... 604/358, 385, 386, 387, 604/389, 393, 397, 406, 407, 402; 206/438, 440, 439, 621, 460; 229/68 R

[56] References Cited

U.S. PATENT DOCUMENTS

| | | | |
|---|---|---|---|
| 3,062,371 | 11/1962 | Patience | 206/440 |
| 3,148,771 | 9/1964 | Miller, Jr. | 206/440 |
| 3,326,480 | 6/1967 | Langdon | 206/438 |
| 3,698,549 | 10/1972 | Glassman | 206/440 |
| 3,717,244 | 2/1973 | Smith | 206/438 |
| 3,973,567 | 8/1976 | Srinivasan | 604/389 |
| 4,182,336 | 1/1980 | Black | 601/585.1 |
| 4,402,689 | 9/1983 | Baum | 604/387 |
| 4,555,022 | 11/1985 | Eagon et al. | 206/440 |
| 4,581,027 | 4/1986 | Alvarado | 604/385.1 |
| 4,605,403 | 8/1986 | Tecker | 604/385.1 |
| 4,608,047 | 8/1986 | Maltingly | 604/387 |
| 4,652,006 | 3/1972 | Trewella | 206/440 |
| 4,692,162 | 9/1987 | Binker et al. | 604/385.1 |
| 4,701,178 | 10/1987 | Glaug et al. | 604/389 |
| 4,735,316 | 4/1988 | Froidh et al. | 604/397 |
| 4,765,477 | 8/1988 | Froidh et al. | 604/358 |
| 4,781,712 | 11/1988 | Barabino et al. | 604/385.1 |

Primary Examiner—Max Hindenburg
Assistant Examiner—K. M. Reichle

[57] ABSTRACT

The present invention is a sanitary napkin, or similar article such as a diaper, which has a flexible, moisture impervious barrier which can also serve as an envelope for maintaining cleanliness of the pad prior to use and/or for discreet and sanitary disposal after use. The barrier comprises a longitudinal envelope having one open edge. This edge has a flap which is normally turned inside the envelope and retained there by one or more areas of pressure sensitive adhesive while the article is in use. The flap can be withdrawn and, while grasping the pad only at the ends, the envelope can be turned inside out to protect the pad or prepare it for disposal. The flap is then pressed down and held by the areas of pressure sensitive adhesive to complete the package.

5 Claims, 3 Drawing Sheets

SANITARY NAPKIN OR LIKE ARTICLE HAVING AN INTEGRAL CARRYING/DISPOSAL ENVELOPE

BACKGROUND OF THE INVENTION

The present invention relates to a sanitary napkin, or a similar article such as a disposable diaper or adult incontinent pad, which comprises a fluid absorbent pad enclosed within a moisture permeable wrapper covering at least one major face and having a flexible mositure impervious barrier essentially covering the other major face of the article. The moisture impervious barrier is formed as a longitudinal envelope which may be used to enclose the pad so as to maintain cleanliness while carrying the article or for sanitary and discreet disposal after use.

The problems associated with sanitary and discreet disposal of single use articles such as diapers and sanitary napkins have been well recognized since their advent. Various proposed solutions to this disposal problem are well documented in the patent literature of the last 35 years. These proposed solutions have followed two general paths. To refer specifically to sanitary napkins, one route has been to enclose the product in a separate bag or envelope which can be retained during use and used later for disposal. A related approach, and apparently the only one which has seen any significant commercial use, is simply to supply an adequate number of disposal bags as entirely separate items included within a package of sanitary napkins. The following U.S. pat. Nos. are exemplary of this approach: Pickens, U.S. Pat. No. 2,750,033; Wallace, U.S. Pat. No. 2,766,927; Srinivasan et al, U.S. Pat. No. 3,973,567; Swanson et al, U.S. Pat. No. 4,556,146; and Newman, U.S. Pat. No. 4,648,513.

Izzo, in United States Pat. No. 4,493,713, shows a disposable diaper supplied with a removal disposal bag covering the body contacting side of the product. This is perforated at each end and must be removed before use. The bag is then retained separately for disposal whether the diaper is changed.

The use of a separate disposal bag or envelope is in most cases quite simple and inexpensive. It does have the disadvantage that the woman using the product must retain the disposal device and have it handy when needed. This is almost always somewhat inconvenient and sometimes impossible. For this reason a second approach has been taken in which an envelope or some other structure intended for later use for disposal is made integral with the pad itself and is retained thereon during use. After use, the soiled pad is totally, or almost so, enclosed within the disposal means before being discarded. In virtually all cases the disposal means is located on the major face of the pad opposite the body facing side. In many cases, although certainly not all, it serves the additional function as a moisture impervious barrier to prevent strikethrough and subsequent soiling of the wearer's clothing.

Evolution of the integral disposal means has followed evolution of sanitary napkins themselves. During the 1970s the tab and belt suspension system in use to that time was superseded by the use of adhesive areas on the back surface of the napkin. These bonded lightly to the undergarments of the wearer to hold the pad in place during use. The nature of suggested integral disposal devices necessarily had to be compatible with this rather basic change in product construction.

The following United States patents can be considered exemplary of attempts at making sanitary napkins with an integral disposal envelope or similar structure. Lane, in U.S. Pat. No. 3,024,788, shows a tab type napkin in which an invertible bag forms one end tab. Elmore, in U.S. Pat. No. 3,035,578, shows a detachable folded flat sheet of moisture impervious material covering the entire garment facing surface of a sanitary napkin. An alternate version includes a separate tucked-in disposal bag inserted in a silt in the napkin wrapper.

Kargul, in U.S. Pat. No. 3,230,956, shows a longitudinal envelope on the garment facing side of a sanitary napkin. This is fan folded along each longitudinal edge and has a centrally located tear strip. Very similar structures are shown by Ryan, in U.S. Pat. No. 4,551,145 and Tucker, U.S. Pat. No. 4,605,403. Tucker also shows a separate embodiment having a tucked-in folded disposal bag very similar to that described earlier by Elmore. Alvarado et al, in U.S. Pat. No. 4,581,027, shows a closely-related structure in which the envelope is not longitudinally pleated but, instead, is wrapped up around each edge of the pad.

Frazer, in U.S. Pat. No. 3,604,423, and Black, in U.S. Pat. No. 4,182,336, shows longitudinally oriented wedged-shaped envelopes made by incorporating triangular side gussets. Black's envelope additionally is transversely fan folded to allow adequate exposure of adhesive strips for bonding the pad to an undergarment.

Robinson, in U.S. Pat. No. 3,274,999, includes a trapezoidal fan folded envelope, similar to those of Black or Frazer, but oriented so as to have the opening parallel to a longitudinal edge of the napkin. The folded envelope is not coextensive with the garment-facing surface and could not effectively prevent strikethrough.

Finally, in the integral envelope group, U.S. Pat. No. 4,402,689 to Baum, should be noted. This uses a simple longitudinal wrap, open at the ends.

U.S. Pat. No. 3,626,945 to Mobley and U.S. Pat. No. 4,380,450 to Reich, might also be mentioned as a third general type of solution to the disposal problem. Each of these sanitary napkins has an adhesive spot located at one end which can be uncovered after use. The soiled napkin is tightly rolled and the adhesive spot serves to retain it in this form.

Of remote relevance to the present invention are U.S. Pat. Nos. 3,096,765 to Cornwell and 3,424,163 to Gravdahl. These principally relate to shields to prevent strike through but neither inventor suggests the use of the shield for later disposal.

Despite the many attempts listed above to provide an answer to the disposal problem, the only approach which has any commercial success to date is the use of an entirely separate wrapper which must then be retained and kept available for disposal after use. The inconvenience of this approach has already been noted, although it does in some cases address one problem which has not heretofore been discussed. This is the matter of a woman who chooses to carry one or more sanitary napkins in her purse, an environment where it almost impossible to maintain them in clean condition unless they are somehow wrapped or packaged. While the separate envelope solves this problem, it does nothing to help with ultimate disposal unless the envelope itself can be retained and kept convenient. To the knowledge of the present inventor, none of the inventions have been commercially successful where a disposal envelope has been made integral with the pad. Further, these do not address the problem of maintaining cleanliness before use.

The present invention is a new and simple approach to maintaining cleanliness of a sanitary napkin or related product prior to use and of providing a simple, convenient, immediately available, discreet and sanitary means for disposing of the product after use.

SUMMARY OF THE INVENTION

The present invention is a sanitary napkin or similar article, such as a disposable diaper or other incontinence product such as an adult pad. It is conventional in that it comprises a fluid absorbent pad enclosed within a moisture permeable wrapper overlying at least one major surface and having a flexible moisture impervious barrier essentially completely covering the other major surface of the article. The moisture impervious barrier comprises an envelope, preferably oriented to have a longitudinal open edge. The term "longitudinal" is used in its conventional sense to refer to the longer dimension of the article while the term "transverse" refers to the shorter dimension. However, it will be understood by those skilled in the art that these terms are relative and should not be considered as limiting in any manner. The envelope has a flap along the open longitudinal edge. This is normally tucked inside and retained there with one or more areas of pressure sensitive adhesive located on the flap. The transverse edges of the envelope are permanently sealed. One major face of the envelope is permanently bonded to a corresponding undergarment facing major face of a sanitary napkin, or the outside face of a like article, using a plurality of fine adhesive lines or other well known method. The other major face of the envelope, in the case the article is a sanitary napkin, can have areas of pressure sensitive adhesive for bonding the article to an undergarment when in use. These adhesive areas are normally covered with a release paper kept in place up to the time of use.

Again using a sanitary napkin as an example, the product would normally be supplied with the envelope flap tucked inside as described above. If a woman wished to maintain the article in clean condition, as while carrying it in a purse, the flap can be readily withdrawn and the envelope turned inside out around the article. The resulting convenient package is sealed by the flap using the same areas of pressure sensitive adhesive which would normally retain it within the envelope. In this case the release paper is retained on those areas of pressure sensitive adhesive used for later bonding the pad to an undergarment. When needed for use, the flap is again released and the package returned to its original configuration. For disposal after use, the same sequence is repeated and the soiled pad is enclosed in a discreet and sanitary package for disposal.

It is an object of the present invention to provide a sanitary napkin or like article having an integral envelope which may be used to maintain the pad in a clean condition prior to use for sanitary disposal after use.

It is another object to provide a sanitary napkin or like article having an integral envelope for protection and/or disposal which is simple and inexpensive to construct using conventional machinery.

These and many other objects will become readily apparent to those skilled in the art upon reading the followed detailed description taken in conjunction with the drawings.

DESCRIPTION OF THE PREFERRED EMBODIMENTS

Figure 1:
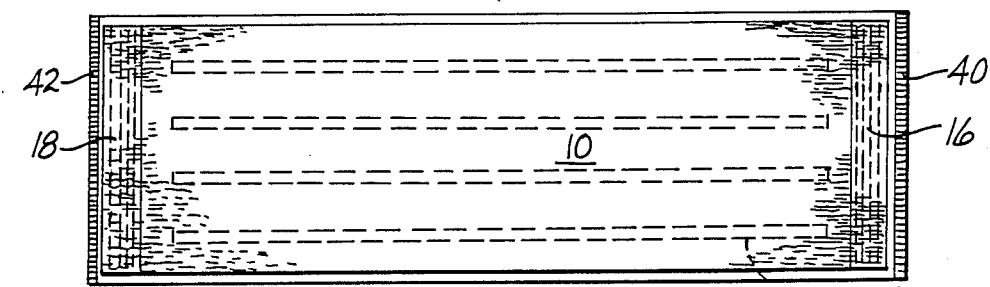
FIG. 1 is a plan view of a sanitary napkin made according to the present invention.
Figure 2:
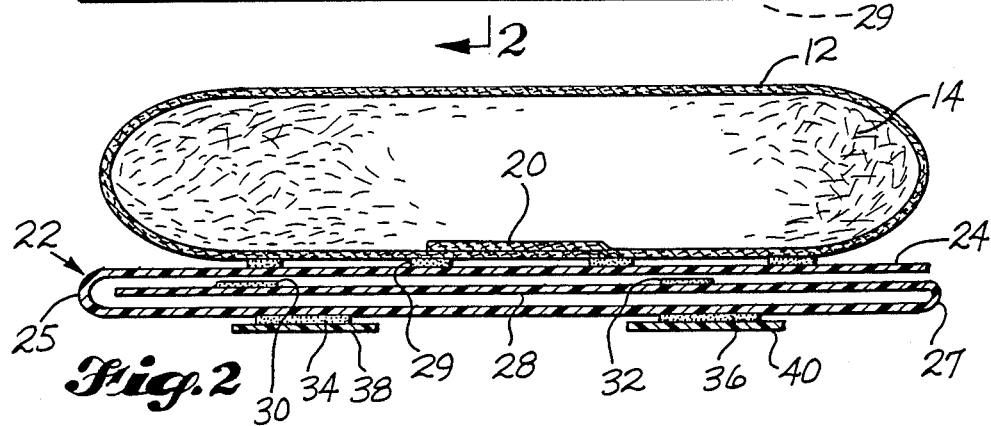
FIG. 2 is a cross section along line 2—2 of FIG. 1.

Reference is now made to the figures for a description of the best mode presently known to the inventor of practicing her invention. A sanitary napkin will be used for convenience of description, although it will be understood that the invention is not limited to an article of this type. In FIGS. 1 and 2 a sanitary napkin 10 has an outer wrapper 12 of a soft nonwoven fabric and an absorbent filler 14. The filler is typically made of a cellulose fluff which may additionally contain particles or areas of a superabsorbent polymer. The fluff pad may be wrapped or enclosed in a tissue layer, not shown here. The ends 16, 18 of the napkin are sealed to retain the filler. In this regard they work in conjunction with a longitudinal overlap 20 where the edges of wrapper 12 meet on the undersurface of the pad. The lower major face of the pad; i.e., the face that lies adjacent to an undergarment during use, is covered with a moisture barrier/envelope generally shown at 22. The pad and envelope are united by a plurality of fine line adhesive strips 29, only one of which is numbered. This has a first ply 24 adjacent to the lower pad surface, a lower ply 26, which is adjacent to the undergarment during use, and a turned in middle ply 28. The middle ply serves as a flap for the envelope. A first longitudinal fold line 25 defines a closed edge of the envelope and a second longitudinal fold line 27 borders the flap and the open edge of the envelope. One or more spots of a pressure sensitive adhesive 30, 32 are placed on flap 28 to maintain it in position and guard against shifting during use of the pad. One or more longitudinal strips 34, 36 of pressure sensitive adhesive are applied to lower ply 26 of the envelope. These serve to lightly bond the pad to an undergarment and retain it in place during wearing. Adhesive strips 34, 36 are covered by release paper 38, 40 which protect them prior to use.

Figure 3:
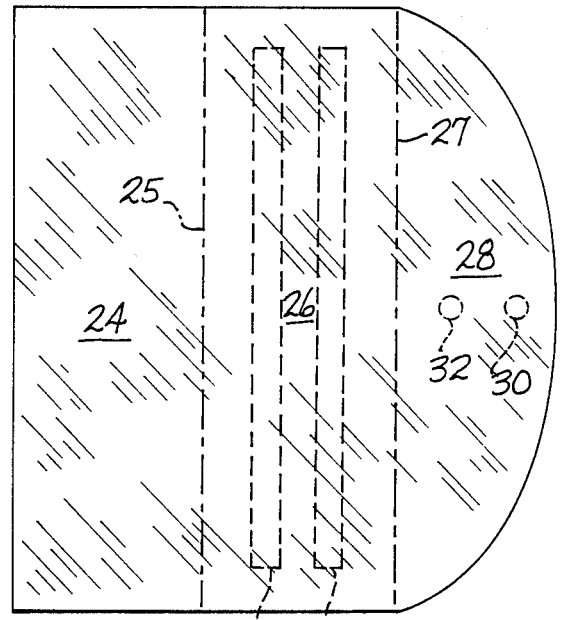
FIG. 3 is a view of the moisture barrier/envelope laid out flat.
Figure 4:
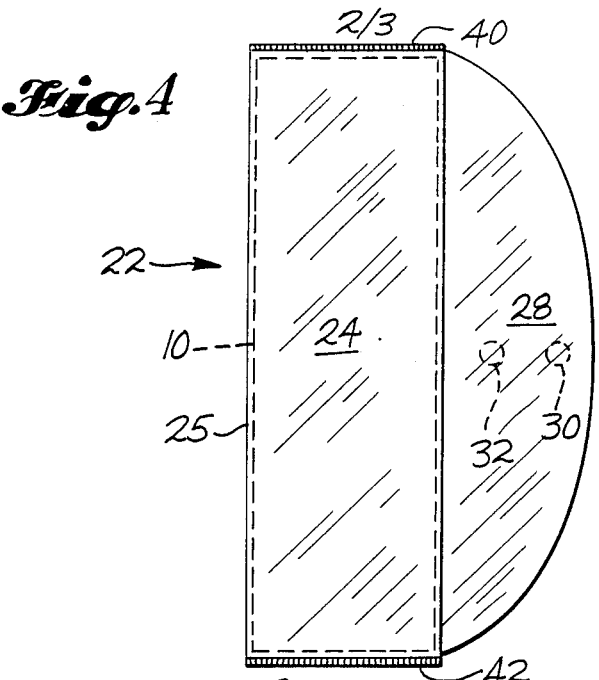
FIG. 4 is a view of the moisture barrier formed into an envelope.

FIGS. 3 and 4 particularly show the construction of the envelope. Here like numerals refer to the same elements as were enumerated above. In FIG. 3 the envelope is in flattened configuration. FIG. 4 shows the now-formed envelope by virtue of being folded along line 25 and having end seals 41, 42. While these may be made separately, preferably they are integral with end seals 16, 18 of the pad itself for simplicity of manufacture. In FIG. 4, flap 28 remains open. The pad itself is shown in outline form on FIG. 4.

Figure 5:
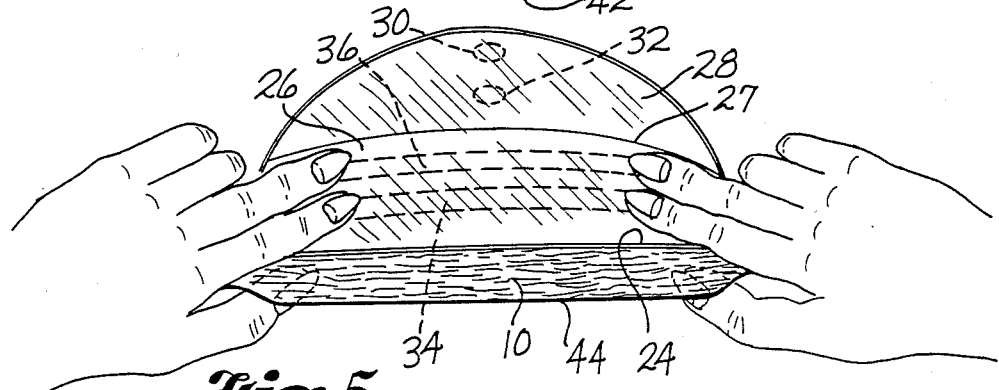
FIG. 5 is a view showing the first step of enclosing the pad within the envelope.
Figure 6:
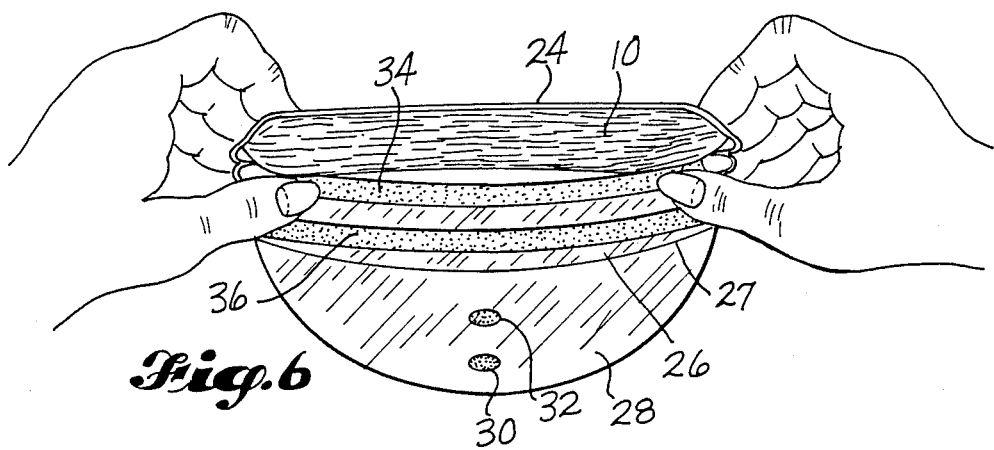
FIG. 6 is a view showing the second step with the pad now essentially enclosed within the envelope.
Figure 7:
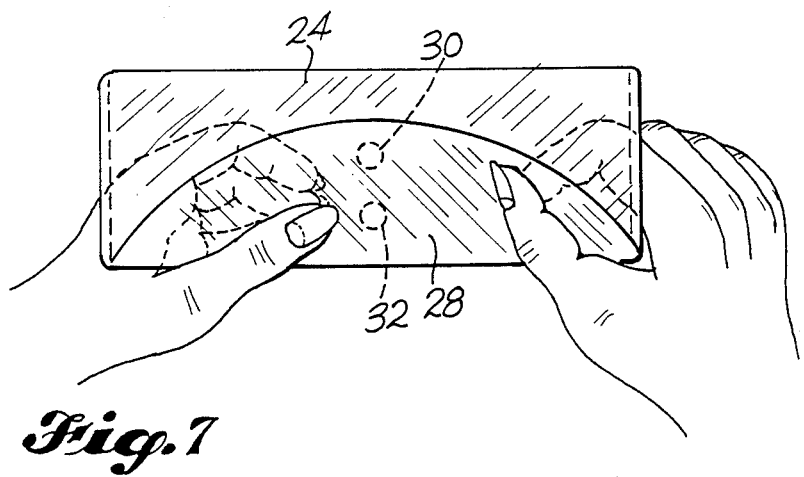
FIG. 7 is a view showing the final step of sealing the pad within the envelope.

The pad would normally be supplied by its manufacturer in the configuration shown in FIGS. 1 and 2; i.e., with the flap tucked inside the envelope and held in place by adhesive spots 30, 32. It may be used directly in this form simply by peeling off the two strips of release paper 38, 40. However, it the user wishes to carry it hygienically in her purse or in some other fashion, flap 28 can be withdrawn from the envelope and the envelope turned inside out to completely cover the sanitary pad as shown in FIGS. 5–7. This is done very simply by first withdrawing flap 28. The pad is then grasped at each end and the index or, more conveniently, the index and middle fingers of each hand inserted into the envelope as shown in FIG. 5. Alternatively, the thumbs can be inserted into the envelope and the outside of the pad gripped by the fingers. The envelope is then turned inside out around the pad as is seen in FIG. 6. Finally, flap 28 is pressed into place and held so by adhesive spots 30, 32 as seen in FIG. 7. The procedure is reversed when the pad is to be made ready for use.

After use, the envelope can be again turned around the soiled pad for disposal. Note, especially in FIG. 5, that it is only necessary to touch the body-contacting surface at the extreme ends of the pad, thus completely avoiding the area that would normally be soiled.

In addition to the advantages already detailed, the present invention is particularly desirable since it can be readily manufactured on standard equipment. Instead of supplying moisture barrier 22 as a flat sheet, the present moisture barrier is supplied in a continuous but prefolded form with adhesive spots 30, 32 already applied.

Having thus outlined the best mode of the present invention, it will be readily apparent to those skilled in the art that many changes can be made without departing from the spirit of the invention. The invention is to be considered as limited only by the following claims.

I claim:

1. A sanitary napkin or like article which comprises a fluid absorbent pad with a moisture permeable wrapper enclosing the pad, said sanitary napkin having a body facing major surface and an opposed undergarment facing major surface, and further having a flexible moisture impervious barrier bonded to and essentially completely covering the undergarment facing surface;

the moisture impervious barrier comprising an envelope having longitudinal and transverse edges with dimensions similar to those of the pad, the transverse edge portions and one longitudinal edge portion of the envelope being permanently sealed, the other longitudinal edge being open, an extending flap being located along said open edge with one or more areas of pressure sensitive adhesive being located on the flap, said flap being normally tucked inside the envelope and retained therein by the adhesive, wherein the flap can be withdrawn from the envelope, the envelope turned inside out to entirely enclose the attached pad, and the flap sealed with the area of pressure sensitive adhesive to close the envelope so as to maintain cleanliness while carrying the article or for sanitary disposal of the article.

2. The article of claim 1 comprising is a sanitary napkin.

3. The article of claim 2 in which the moisture impervious barrier envelope has one major outside surface bonded to the pad and wrapper assembly and has at least one area of pressure sensitive adhesive on the other major outside surface for holding the article to an undergarment when in use.

4. The article of claim 1 comprising is a disposable diaper.

5. The article of claim 1 comprising is an adult incontinent pad.

* * * * *